United States Patent [19]

Higashio et al.

[11] Patent Number: 4,684,758

[45] Date of Patent: Aug. 4, 1987

[54] PRODUCTION OF 2,5-DIMETHYL-2,4-HEXADIENE

[75] Inventors: Yasuhiko Higashio; Kazuteru Takahashi, both of Ichihara, Japan

[73] Assignee: Sumitomo Chemical Company, Ltd., Osaka, Japan

[21] Appl. No.: 891,173

[22] Filed: Jul. 31, 1986

[30] Foreign Application Priority Data

| Aug. 7, 1985 [JP] | Japan | 60-173815 |
| Dec. 27, 1985 [JP] | Japan | 60-297283 |
| Feb. 3, 1986 [JP] | Japan | 61-21697 |
| Apr. 30, 1986 [JP] | Japan | 61-101324 |

[51] Int. Cl.$^4$ .......... C07C 1/20; C07C 11/12
[52] U.S. Cl. .................. 585/608; 585/606; 585/609
[58] Field of Search ............ 585/603, 606, 608, 607, 585/609

[56] References Cited

U.S. PATENT DOCUMENTS

| 3,692,743 | 9/1972 | Thompson | 585/606 |
| 3,856,882 | 12/1974 | Takagi et al. | 585/608 |
| 4,507,518 | 3/1985 | Petroline et al. | 585/610 |

FOREIGN PATENT DOCUMENTS

| 229877 | 12/1958 | Australia | 585/608 |
| 225643 | 12/1958 | Australia | 585/608 |
| 239966 | 1/1960 | Australia | 585/608 |
| 9005906 | 1/1974 | Japan | 585/607 |
| 9018804 | 2/1974 | Japan | 585/608 |
| 9018803 | 2/1974 | Japan | 585/608 |

OTHER PUBLICATIONS

Chemical Abstract, 96:217223a (1982).

*Primary Examiner*—Asok Pal
*Attorney, Agent, or Firm*—Antonelli, Terry & Wands

[57] ABSTRACT

2,5-Dimethyl-2,4-hexadiene which is an intermediate for preparing agricultural chemicals, insecticides or medicines, is prepared by bringing isobutylene and/or tert.-butyl alcohol into contact with isobutyl aldehyde in a gaseous phase at a temperature of 150°–350° C. in the presence of a niobic acid catalyst.

7 Claims, No Drawings

PRODUCTION OF 2,5-DIMETHYL-2,4-HEXADIENE

This invention relates to an improvement in production of 2,5-dimethyl-2,4-hexadiene by a reaction between isobutylene and/or tert.-butyl alcohol and isobutyl aldehyde.

2,5-dimethyl-2,4-hexadiene is useful as intermediates for agricultural chemicals, insecticides, medicines and other organic synthesis. A method for preparing 2,5-dimethyl-2,4-hexadiene from isobutylene and/or tert.-butyl alcohol with isobutyl aldehyde is proposed wherein the reactants are allowed to react under pressure in a liquid phase in the presence of mineral acids, sulfonic acid, heteropoly acids (Japanese Patent Kokai No. 48-34108). The method is not satisfactory, since yield of 2,5-dimethyl-2,4-hexadiene is as small as less than 40%, accompanying with a large amount of by-products, and paying attention is needed to corrosion of an apparatus owing to mineral acids or sulfonic acid.

After extensive study to dissolve the difficulties above, the present inventors find that the reaction between isobutylene and/or tert.-butyl alcohol and isobutyl aldehyde should be conducted in a gaseous phase in the presence of a niobic acid catalyst at a temperature of 150°–350° C.

According to the present invention, isobutylene and/or tert.-butyl alcohol is brought into contact with isobutyl aldehyde in a gaseous phase at a temperature of 150°–350° C. in the presence of a niobic acid catalyst.

Materials are isobutylene, tert.-butyl alcohol and isobutyl aldehyde. There is no critical restriction to any materials. So far as isobutylene is concerned, highly pure one may be used as it is or so-called "spent B-B fraction" may also be used. Isobutylene may be fed in the form of a mixture with tert.-butyl alcohol.

There is no critical limitation in a mixing ratio of isobutylene or tert.-butyl alcohol to isobutyl aldehyde or of a mixture of isobutylene and tert.-butyl alcohol to isobutyl aldehyde. Preferable ratio of isobutylene or tert.-butyl alcohol or a mixture of isobutylene and tert.-butyl alcohol to isobutyl aldehyde is 1–10:1 in mol.

Preferable catalyst is niobic acid whose max. acidity is stronger than −5.6 in terms of Ho-function, more preferably, niobic acid which is called as hydrous niobium oxide. Preparation of niobic acid is disclosed, for example, in Japanese Patent Kokai No 60-44039.

The niobic acid catalyst may be used as it is, but preferably, is pre-treated with mineral acid such as sulfuric acid or phosphoric acid. Pre-treatment with mineral acid is effected in such a manner that the niobic acid is dipped in aqueous mineral acid solution and then washed with water. Alternatively, the aqueous mineral acid solution is flowed through a tower in which niobic acid is packed and then the tower is washed with water. Mineral acid is, preferably, sulfuric acid and phosphoric acid. Concentration of the acid solution varies according to conditions of the pre-treatment, but is usually 0.01–1.0 mol per liter. An amount of the acid solution employed is usually 2–10 times in volume as much as niobic acid. Niobic acid thus pre-treated is calcined usually at a temperature of 100°–500° C. before it is used as a catalyst.

Niobic acid catalyst pre-treated above is more active and has higher selectivity of 2,5-dimethyl-2,4-hexadiene than non-pre-treated one. The use of thus pre-treated catalyst is able to increase yield of 2,5-dimethyl-2,4-hexadiene.

The present reaction is carried out in a gaseous phase and at a temperature of 150°–350° C., preferably 200°–300° C. Reaction at a temperature higher than 350° C. is accompanied with a large amount of higher-boiling products such as polymers, while that at a temperature lower than 150° C. brings about decrease in reaction speed. Any pressure may be employed as long as the reaction system is kept at a gaseous phase, usually at atmospheric pressure or higher, preferably 2–10 atm (absolute).

The present reaction is carried usually out in a fixed-bed catalytic reactor wherein the materials are continuously fed in a reactor in which the solid catalyst is packed.

Alternatively, the reaction may be carried out in a fluidizer reactor.

EXAMPLES

Example 1

A tubular reactor made of quartz (inner diameter: 17 mm) was packed with niobic acid catalyst (20 ml, manufacturer: CBMM Co.) and heated to 250° C. in an electric furnace. Isobutylene and isobutyl aldehyde were charged therein at rates of 22.4 g/hr and 14.4 g/hr., respectively, and the reaction was effected under atmospheric pressure. Gas discharged was cooled with ice water and light boiling compounds such as unaltered isobutylene was further cooled with dry-methanol. Reaction liquid thus obtained was assayed by gas-chromatography to calculate conversion of isobutyl aldehyde (hereinafter referred to as "conversion") (%), selectivity of 2,5-dimethyl-2,4-hexadiene (hereinafter referred to as "selectivity") (%) and yield of 2,5-dimethyl-2,4-hexadiene (hereinafter referred to as "yield") (%), all being based on isobutyl aldehyde (mol). The values hereinafter are those at the eighth hour after the reaction initiates, unless otherwise defined.

Conversion 89.3%
Selectivity 65.3%
Yield 58.3%

Examples 2–5 and Comparison example 1

Example 1s were repeated except that reaction temperatures and charging rates of isobutylene and isobutyl aldehyde were changed as shown in Table 1. Results are shown in Table 1.

TABLE 1

| | Temperatures (°C.) | Isobutylene (g/hr) | Isobutyl aldehyde (g/hr) | Conversion (%) | Selectivity (%) | Yield (%) |
|---|---|---|---|---|---|---|
| Example 2 | 320 | 44.8 | 28.8 | 97.3 | 58.4 | 56.9 |
| Example 3 | 180 | 11.2 | 7.2 | 81.3 | 64.4 | 52.3 |
| Example 4 | 250 | 44.8 | 14.4 | 93.3 | 68.1 | 63.5 |
| Example 5 | 250 | 11.2 | 14.4 | 80.9 | 58.8 | 47.6 |
| Comparison example 1 | 130 | 11.2 | 7.2 | 32.1 | 40.8 | 13.1 |

Example 6

Example 1 was repeated except that tert.-butyl alcohol (29.6 g/hr) was charged in place of isobutylene (22.4 g/hr).
Conversion 65.3%
Selectivity 65.2%
Yield 42.4%

Example 7

A tubular reactor made of SUS (inner diameter=23 mm) was packed with niobic acid catalyst (20 ml, manufacturer: CBMM Co.) and heated to 250° C. in an electric furnace. Isobutylene and isobutyl aldehyde were charged therein at rates of 44.8 g/hr and 14.4 g/hr, respectively, and the reaction was effected under pressure (5 Kg/cm$^2$ gauge). Gas discharged was de-pressurized to the atmospheric pressure and then cooled with dry ice-methanol. The reaction liquid was assayed by gas-chromatography.
Conversion 95.3%
Selectivity 79.5%
Yield 75.8%

No formation of diisobutylene was observed, and almost all excess isobutylene was recovered.

The reaction was further continued until 300 hours was passed since the reaction initiated;
Conversion (300th) 92.1%
Selectivity (300th) 78.9%
Yield (300th) 72.7%
Little degradation of catalytic activity was seen.

Examples 8–11

Example 10s were repeated except that reaction temperatures and pressures were changed as in Table 2. Results are shown in Table 2.

TABLE 2

| | Temperature (°C.) | Pressure (Kg/cm$^2$ Gauge) | Conversion (%) | Selectivity (%) | Yield (%) |
|---|---|---|---|---|---|
| Example 8 | 300 | 5.0 | 98.8 | 71.6 | 70.8 |
| Example 9 | 200 | 5.0 | 81.4 | 68.8 | 56.3 |
| Example 10 | 250 | 10.0 | 96.6 | 71.9 | 69.5 |
| Example 11 | 250 | 0 | 92.9 | 67.2 | 62.4 |

Example 12

Example 7 was repeated except that tert.-butyl alcohol (59.2 g/hr) was charged in place of isobutylene (44.8 g/hr).
Conversion 69.6%
Selectivity 68.8%
Yield 48.2%

Example 13

Niobic acid catalyst pre-treated with phosphoric acid was prepared as follows.

Niobic acid (100 ml, manufacturer: CBMM Co.) was dipped for two hours at room temperature in 0.1 N/liter aqueous phosphoric acid solution (500 ml). Then, the niobic acid was repeatedly washed (five times) with pure water (1 liter), and calcined for four hours at 350° C.

A tubular reactor made of SUS (inner diameter=23 mm) was packed with the niobic acid catalyst pre-treated above (20 ml) and heated to 250° C. in an electric furnace. Isobutylene and isobutyl aldehyde were charged therein at rates of 44.8 g/hr and 14.4 g/hr, respectively, and a reaction was effected under pressure (5 Kg/cm$^2$ gauge). Gas discharged was de-pressurized to the atmospheric pressure and then cooled, with dry ice-methanol, before it was assayed by gas-chromatography.
Conversion 97.8%
Selectivity 83.3%
Yield 81.6%

The reaction was further continued until 300 hours was passed since the reaction initiated:
Conversion (300th) 93.2%
Selectivity (300th) 83.9%
Yield (300th) 78.2%
Little degradation in catalytic acitivity and selectivity was seen.

Examples 14–16

Example 13 was repeated except that reaction temperatures and pressures were changed as in Table 3. Results are shown in Table 3.

TABLE 3

| | Temperature (°C.) | Pressure (Kg/cm$^2$ Gauge) | Conversion (%) | Selectivity (%) | Yield (%) |
|---|---|---|---|---|---|
| Example 14 | 300 | 5.0 | 99.1 | 77.4 | 76.9 |
| Example 15 | 250 | 10.0 | 98.5 | 75.5 | 74.4 |
| Example 16 | 250 | 0 | 95.3 | 71.9 | 68.5 |

Example 17

Example 13 was repeated except that tert.-butyl alcohol (59.2 g/hr) was charged in place of isobutylene (44.8 g/hr).
Conversion 79.4%
Selectivity 80.4%
Yield 63.8%

Example 18

Niobic acid catalyst pre-treated with sulfuric acid was prepared as follows:

Niobic acid (100 ml, manufacturer: CBMM Co.) was dipped for two hours at room temperature in 0.1 mol/liter aqueous sulfuric acid solution (500 ml). The niobic acid was repeatedly washed (five times) with pure water (1 liter) and calcined for four hours at 350° C.

A tubular reactor made of SUS (inner diameter: 23 mm) was packed with the niobic acid catalyst pre-treated above (20 ml) and heated to 250° C. in an electric furnace. Isobutylene and isobutyl aldehyde were charged therein at rates of 44.8 g/hr. and 14.4 g/hr, respectively, and reaction was effected under pressure (5 Kg/cm$^2$ gauge). Gas discharged was depressurized to the atmospheric pressure and cooled with dry ice-methanol, before the gas was assayed by gas-chromatography.
Conversion 96.6%
Selectivity 83.3%
Yield 80.5%

The reaction was further continued until 300 hours was passed since the reaction initiated.
Conversion (300th) 94.1%

Selectivity (300th) 84.1%

Yield (300th) 79.1%

Little degradation in catalytic activity and selectivity was seen.

Example 19-21

Example 18 was repeated except that reaction temperatures and pressures were changed as in Table 4. Results are shown in Table 4.

TABLE 4

| | Temperature (°C.) | Pressure (Kg/cm² Gauge) | Conversion (%) | Selectivity (%) | Yield (%) |
|---|---|---|---|---|---|
| Example 19 | 300 | 5.0 | 98.9 | 79.3 | 78.4 |
| Example 20 | 250 | 10.0 | 97.6 | 79.8 | 77.9 |
| Example 21 | 250 | 0 | 95.2 | 73.8 | 70.3 |

Example 22

Example 18 was repeated except that tert.-butyl alcohol (59.2 g/hr) was charged in place of the isobutylene (44.8 g/hr).
Conversion 80.4%
Selectivity 82.6%
Yield 66.4%

We claim:

1. A method for preparing 2,5-dimethyl-2,4-hexadiene by bringing isobutylene and/or tert.-butyl alcohol into contact with isobutyl aldehyde in a gaseous phase in the presence of a niobic acid catalyst at a temperature of 150°-350° C.

2. A method according to claim 1 wherein isobutylene or tert.-butyl alcohol or a mixture thereof to isobutyl aldehyde is 1-10:1 in mol.

3. A method according to claim 1 wherein the catalyst is niobic acid pre-treated with mineral acid.

4. A method according to claim 3 wherein the mineral acid is sulfuric acid or phosphoric acid.

5. A method according to claim 1 wherein the contact is effected under pressure.

6. A method according to claim 1 wherein the contact is effected at atmospheric pressure.

7. A method according to claim 1 wherein the contact is effected at a temperature of 200°-350° C.

* * * * *